United States Patent
Kneip et al.

(10) Patent No.: US 8,330,579 B2
(45) Date of Patent: *Dec. 11, 2012

(54) RADIO-FREQUENCY AUTO-IDENTIFICATION SYSTEM FOR DIALYSIS SYSTEMS

(75) Inventors: Daniel Kneip, Anna, TX (US); David West, Richardson, TX (US); David Cummings, Richardson, TX (US); Patrick Lee, Long Grove, IL (US); Randy Murphy, Pleasant Prairie, WI (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1149 days.

This patent is subject to a terminal disclaimer.

(21) Appl. No.: 11/773,822

(22) Filed: Jul. 5, 2007

(65) Prior Publication Data

US 2009/0009290 A1 Jan. 8, 2009

(51) Int. Cl.
*H04Q 5/22* (2006.01)
(52) U.S. Cl. .......................... 340/10.1; 604/29
(58) Field of Classification Search .......... 455/562.1; 340/10.1, 572.1; 604/29, 533–536, 538
See application file for complete search history.

(56) References Cited

U.S. PATENT DOCUMENTS

| | | | |
|---|---|---|---|
| 3,570,495 A | 3/1971 | Wright | |
| 4,541,829 A * | 9/1985 | Munsch et al. | 604/80 |
| 4,655,753 A * | 4/1987 | Bellotti et al. | 604/534 |
| 4,694,409 A | 9/1987 | Lehman | |
| 4,857,713 A | 8/1989 | Brown | |
| 4,869,286 A | 9/1989 | Williams et al. | |
| 5,069,219 A | 12/1991 | Knoblich | |
| 5,164,575 A | 11/1992 | Neeley et al. | |
| 5,174,281 A | 12/1992 | Lee | |
| 5,193,549 A | 3/1993 | Bellin et al. | |
| 5,311,899 A | 5/1994 | Isayama et al. | |
| 5,389,771 A | 2/1995 | Amendolia | |
| 5,518,021 A | 5/1996 | Benimeli | |
| 5,540,265 A | 7/1996 | Polaschegg et al. | |
| 5,572,992 A | 11/1996 | Kankkunen et al. | |
| 5,583,948 A | 12/1996 | Shibayama | |

(Continued)

FOREIGN PATENT DOCUMENTS

| | | |
|---|---|---|
| DE | 100 05 108 | 8/2001 |
| DE | 20 2005 016276 | 12/2005 |
| EP | 0311848 | 4/1989 |

(Continued)

OTHER PUBLICATIONS

International Search Report and Written Opinion for International Application No. PCT/US2008/068950 mailed on May 7, 2009.

*Primary Examiner* — Brian Zimmerman
*Assistant Examiner* — An T Nguyen
(74) *Attorney, Agent, or Firm* — K&L Gates LLP (57) ABSTRACT

A medical fluid delivery system includes a dialysis instrument; a disposable pumping cassette operable with a pumping actuator of the dialysis instrument, the disposable cassette including or connected fluidly to a plurality of first connectors; a plurality of second connectors configured to interface with the first connectors, each second connector associated with a radio frequency ("RFID") tag; and electronics configured to read the RFID tags via a plurality of antennae and to identify that each of the second connectors is positioned properly with respect to a proper one of the first connectors.

26 Claims, 8 Drawing Sheets

U.S. PATENT DOCUMENTS

| | | | |
|---|---|---|---|
| 5,681,339 A | 10/1997 | McEwen et al. | |
| 5,741,294 A | 4/1998 | Stromberg | |
| 5,830,164 A | 11/1998 | Cone et al. | |
| 5,842,976 A | 12/1998 | Williamson | |
| 5,876,359 A | 3/1999 | Bock et al. | |
| 5,910,776 A | 6/1999 | Black | |
| 5,925,014 A | 7/1999 | Teeple Jr. | |
| 5,938,634 A | 8/1999 | Packard | |
| 5,945,651 A | 8/1999 | Chorosinski et al. | |
| 5,966,083 A | 10/1999 | Marsh et al. | |
| 5,986,562 A | 11/1999 | Nikolich | |
| 6,070,687 A | 6/2000 | Wallace et al. | |
| 6,148,888 A | 11/2000 | Benimeli | |
| 6,260,049 B1 | 7/2001 | Fitzgerald et al. | |
| 6,293,921 B1 * | 9/2001 | Shinmoto et al. | 604/29 |
| 6,335,686 B1 | 1/2002 | Goff et al. | |
| 6,361,548 B1 | 3/2002 | McEwen | |
| 6,400,272 B1 | 6/2002 | Holtzman et al. | |
| 6,441,736 B1 | 8/2002 | Leighton | |
| 6,441,741 B1 | 8/2002 | Yoakum | |
| 6,468,424 B1 | 10/2002 | Donig et al. | |
| 6,588,670 B2 | 7/2003 | Bukowski | |
| 6,600,420 B2 | 7/2003 | Goff et al. | |
| 6,637,649 B2 | 10/2003 | Walsh | |
| 6,670,885 B2 | 12/2003 | Kosaka | |
| 6,685,678 B2 | 2/2004 | Evans et al. | |
| 6,726,099 B2 | 4/2004 | Becker et al. | |
| 6,758,802 B2 | 7/2004 | Fitzgerald et al. | |
| 6,830,180 B2 | 12/2004 | Walsh | |
| 6,853,087 B2 | 2/2005 | Neuhaus et al. | |
| 6,853,303 B2 | 2/2005 | Chen et al. | |
| 6,861,954 B2 | 3/2005 | Levin | |
| 6,884,255 B1 | 4/2005 | Newton | |
| 6,910,626 B2 | 6/2005 | Walsh | |
| 6,935,560 B2 | 8/2005 | Andreasson et al. | |
| 6,940,408 B2 | 9/2005 | Ferguson et al. | |
| 6,951,596 B2 | 10/2005 | Green et al. | |
| 6,967,563 B2 | 11/2005 | Bormaster | |
| 6,967,577 B2 | 11/2005 | Taylor et al. | |
| 6,975,205 B1 | 12/2005 | French et al. | |
| 6,976,628 B2 | 12/2005 | Krupa | |
| 7,005,964 B2 | 2/2006 | Edmonson et al. | |
| 7,005,968 B1 | 2/2006 | Bridgelall | |
| 7,009,561 B2 | 3/2006 | Menache et al. | |
| 7,017,822 B2 | 3/2006 | Aisenbrey | |
| 7,019,618 B2 | 3/2006 | Pratt et al. | |
| 7,019,639 B2 | 3/2006 | Stilp | |
| 7,019,650 B2 | 3/2006 | Volpi et al. | |
| 7,023,341 B2 | 4/2006 | Stilp | |
| 7,041,941 B2 | 5/2006 | Faries, Jr. et al. | |
| 7,044,381 B2 | 5/2006 | Silverbrook et al. | |
| 7,053,764 B2 | 5/2006 | Stilp | |
| 7,057,512 B2 | 6/2006 | Stilp | |
| 7,061,379 B2 | 6/2006 | Chen et al. | |
| 7,074,209 B2 | 7/2006 | Evans et al. | |
| 7,079,034 B2 | 7/2006 | Stilp | |
| 7,083,106 B2 | 8/2006 | Albany | |
| 7,084,740 B2 | 8/2006 | Bridgelall | |
| 7,091,827 B2 | 8/2006 | Stilp | |
| 7,091,861 B2 | 8/2006 | Schmidtberg et al. | |
| 7,102,520 B2 | 9/2006 | Liu et al. | |
| 7,108,184 B2 | 9/2006 | Mase et al. | |
| 7,115,113 B2 | 10/2006 | Evans et al. | |
| 7,116,228 B1 | 10/2006 | Singleton | |
| 7,118,029 B2 | 10/2006 | Nycz et al. | |
| 7,119,692 B2 | 10/2006 | Lieffort et al. | |
| 7,125,382 B2 | 10/2006 | Zhou et al. | |
| 7,130,773 B1 | 10/2006 | Wong | |
| 7,132,946 B2 | 11/2006 | Waldner et al. | |
| 7,140,542 B2 | 11/2006 | Andreasson et al. | |
| 7,142,118 B2 | 11/2006 | Hamilton et al. | |
| 7,148,803 B2 | 12/2006 | Bandy et al. | |
| 7,150,399 B2 | 12/2006 | Barrus et al. | |
| 7,151,454 B2 | 12/2006 | Washington | |
| 7,154,378 B1 | 12/2006 | Ertas et al. | |
| 7,155,172 B2 | 12/2006 | Scott | |
| 7,156,312 B2 | 1/2007 | Becker et al. | |
| 7,170,415 B2 | 1/2007 | Forster | |
| 7,175,081 B2 | 2/2007 | Andreasson et al. | |
| 7,178,416 B2 | 2/2007 | Whelan et al. | |
| 7,182,256 B2 | 2/2007 | Andreasson et al. | |
| 7,187,288 B2 | 3/2007 | Mendolia et al. | |
| 7,209,042 B2 | 4/2007 | Martin et al. | |
| 7,213,760 B2 | 5/2007 | Mase et al. | |
| 7,213,767 B2 | 5/2007 | Tethrake et al. | |
| 7,214,224 B2 | 5/2007 | Goble | |
| 7,215,976 B2 | 5/2007 | Brideglall | |
| 7,218,231 B2 | 5/2007 | Higham | |
| 7,218,232 B2 | 5/2007 | DiSilvestro et al. | |
| 7,224,280 B2 | 5/2007 | Ferguson et al. | |
| 7,227,469 B2 | 6/2007 | Varner et al. | |
| 7,232,066 B2 | 6/2007 | Andreasson et al. | |
| 7,233,247 B1 | 6/2007 | Crossno et al. | |
| 7,234,801 B2 | 6/2007 | Silverbrook | |
| 7,239,229 B2 | 7/2007 | Bauhahn | |
| 7,240,833 B2 | 7/2007 | Zarembo | |
| 7,240,848 B1 | 7/2007 | Dressen et al. | |
| 7,241,266 B2 | 7/2007 | Zhou et al. | |
| 7,242,293 B2 | 7/2007 | Rea et al. | |
| 7,242,301 B2 | 7/2007 | August et al. | |
| 7,243,002 B1 | 7/2007 | Hoganson et al. | |
| 7,246,744 B2 | 7/2007 | O'Brien et al. | |
| 7,248,160 B2 | 7/2007 | Mangan et al. | |
| 7,248,171 B2 | 7/2007 | Mishelevich | |
| 7,253,717 B2 | 8/2007 | Armstrong et al. | |
| 7,253,736 B2 | 8/2007 | Tethrake et al. | |
| 7,256,696 B2 | 8/2007 | Levin | |
| 7,256,699 B2 | 8/2007 | Tethrake et al. | |
| 7,260,369 B2 | 8/2007 | Feher | |
| 7,268,680 B2 | 9/2007 | Gary, Jr. | |
| 7,268,684 B2 | 9/2007 | Tethrake et al. | |
| 7,268,687 B2 | 9/2007 | Egbert et al. | |
| 7,276,675 B2 | 10/2007 | Faries, Jr. et al. | |
| 7,289,066 B2 | 10/2007 | Homolle et al. | |
| 7,295,120 B2 | 11/2007 | Waldner et al. | |
| 7,297,112 B2 | 11/2007 | Zhou et al. | |
| 7,298,243 B2 | 11/2007 | Juels et al. | |
| 7,304,577 B2 | 12/2007 | Waldner et al. | |
| 7,304,578 B1 | 12/2007 | Sayers et al. | |
| 7,306,197 B2 * | 12/2007 | Parrino et al. | 251/149.6 |
| 7,307,245 B2 | 12/2007 | Faries, Jr. et al. | |
| 7,316,358 B2 | 1/2008 | Kotik et al. | |
| 7,319,396 B2 | 1/2008 | Homanfar et al. | |
| 7,319,397 B2 | 1/2008 | Chung et al. | |
| 7,319,398 B2 | 1/2008 | Marino | |
| 7,322,514 B2 | 1/2008 | Lubow | |
| 7,736,328 B2 * | 6/2010 | Childers et al. | 604/29 |
| 7,955,295 B2 * | 6/2011 | Lee et al. | 604/29 |
| 8,083,709 B2 * | 12/2011 | Childers et al. | 604/29 |
| 2001/0040127 A1 | 11/2001 | Donig et al. | |
| 2002/0188259 A1 * | 12/2002 | Hickle et al. | 604/189 |
| 2003/0141009 A1 * | 7/2003 | Landherr et al. | 156/158 |
| 2004/0193453 A1 * | 9/2004 | Butterfield et al. | 705/2 |
| 2005/0277890 A1 | 12/2005 | Stewart et al. | |
| 2006/0224128 A1 * | 10/2006 | Lurvey et al. | 604/250 |
| 2006/0265246 A1 * | 11/2006 | Hoag | 705/2 |
| 2007/0106247 A1 * | 5/2007 | Burnett et al. | 604/508 |
| 2007/0213684 A1 * | 9/2007 | Hickle et al. | 604/500 |
| 2007/0253463 A1 * | 11/2007 | Perry et al. | 374/208 |
| 2008/0015493 A1 * | 1/2008 | Childers et al. | 604/29 |
| 2008/0015494 A1 * | 1/2008 | Santini et al. | 604/65 |
| 2008/0058697 A1 * | 3/2008 | Kamen et al. | 604/6.13 |
| 2008/0175719 A1 * | 7/2008 | Tracey et al. | 417/38 |
| 2009/0012448 A1 * | 1/2009 | Childers et al. | 604/29 |
| 2009/0012449 A1 * | 1/2009 | Lee et al. | 604/29 |
| 2009/0299272 A1 * | 12/2009 | Hopping et al. | 604/29 |
| 2011/0092894 A1 * | 4/2011 | McGill et al. | 604/29 |

FOREIGN PATENT DOCUMENTS

| | | |
|---|---|---|
| EP | 0575970 | 12/1993 |
| EP | 1 872 814 | 1/2008 |
| WO | WO 92/11046 | 7/1992 |
| WO | WO 96/25214 | 8/1996 |
| WO | WO 2006/036600 | 4/2006 |

* cited by examiner

RADIO-FREQUENCY AUTO-IDENTIFICATION SYSTEM FOR DIALYSIS SYSTEMS

BACKGROUND

The present disclosure relates generally to healthcare/medication delivery systems and more specifically to identifying and locating medical connectors and fluids used in healthcare/medication delivery systems using radio frequency identification ("RFID") technology.

Complex medical fluids are often administered to a patient through a variety of different medication delivery systems. For example, a medication delivery system such as a dialysis machine for performing peritoneal dialysis or hemodialysis on a patient having decreased or total loss of kidney function uses a dialysis solution or dialysate that removes waste from the patient's bloodstream. In another example, infusion pumps for medication delivery deliver liquid drugs or medical fluids, such as morphine or the like to a patient based upon parameters entered into the medication delivery system. The above fluids can be a homogenous liquid, a mixed solution or a solution that includes particulates in a buffer liquid.

The concentration or presence of the medication in the solution being delivered to a patient is important because an improper dose or the administration of the wrong drug can cause serious problems. A problem associated with peritoneal dialysis, for example, is an improperly mixed or non-mixed solution being delivered to a patient. Certain types of dialysate are packaged in dual-chamber bags in which one chamber includes a buffer solution and the other chamber includes a concentrated glucose solution. The chambers of the bag are separated by a peelable or frangible seal that the patient or caregiver ruptures to open. The pH value of either the buffer solution and the glucose solution is such that the liquids alone are potentially harmful to the patient. The resulting pH value of the two fluids properly mixed however is suitable for injection into the patient's peritoneum. With peritoneal dialysis, therefore, it is desirable to make sure that the peelable or frangible seal is ruptured so that the resulting solution is mixed properly.

Certain dialysates, such as those used in hemodialysis, are bicarbonate-based. Bicarbonate is unstable in the presence of magnesium and calcium and forms a precipitate after a period of time. Here, premature mixing of the bicarbonate and contents of adjacent chambers may have deleterious effects on the resulting combination or render the combination of contents useless after an extended time. Bicarbonate alone can also be physiologically unsafe for the patient. Accordingly, it is necessary to properly mix the bicarbonate and other solution to form a final solution before contacting any solution with the patient's blood. With hemodialysis, therefore, it is also desirable to ensure that solution has been mixed timely and properly.

Again, with any medical fluid injection, it is important to know that the proper type and dose of a drug or medical fluid is being infused into a patient.

SUMMARY

The present disclosure includes a positional radio frequency identification ("RFID") auto-identification system for medication delivery systems. The RFID system provides positional information for a medical connector using RFID technology based on the location of the medical connector, and its associated RFID tag, with respect to a medication delivery system. The RFID system also reads information encoded on the RFID tag associated with the medical connector. The RFID system may also provide information regarding a disposable medical apparatus and its associated RFID tag.

The RFID system, in an embodiment, is operable with a medical instrument, which includes pumping and valving actuators that drive pump and valve chambers of a disposable cassette. The medical instrument is a dialysis instrument in one embodiment. The cassette can also have supply ports, which connect to connectors at the end of supply fluid lines. The cassette can also have ports that connect to connectors for a drain line, patient line and warmer bag line. Each of the medical connectors in one embodiment includes an RFID tag.

The system also includes electronics configured to read the RFID tags of the medical connectors using a number of antennae. The electronics identify that each of the medical connectors will be connected to a proper one of the ports. The antennae are positioned at least a maximum read distance of the RFID tags apart. Each antenna is also associated with and positioned less than the maximum read distance from a dedicated port. Alternatively, each antenna can also be positioned within an operating distance from a dedicated port.

The electronics may include an integrated circuit, e.g., provided on a printed circuit board, which is configured to the read RFID tags. The integrated circuit can include an RFID interrogator or reader, which can be in communication with the antennae through a multiplexer or which can communicate directly or indirectly with the antennae without a multiplexer.

At least one of the RFID tags, in an embodiment, is encoded with information. Such information can relate to the type of a solution contained in a corresponding container or bag, volume of such bag, or whether the connector is a patient line connector, a drain line connector or a warmer bag connector. The information may be encrypted. The disposable cassette, in an embodiment, includes an RFID tag encoded with information regarding the disposable cassette. The information regarding the disposable cassette may also be encrypted, such that third party cassettes can be detected and not used.

The cassette RFID tag allows the instrument to operate with different cassettes and to know which cassette has been loaded into the instrument. Once the instrument knows which cassette is loaded, the tags on the connectors connected to the cassette tell the instrument if the proper connections have been made for the particular cassette. In an alternative embodiment, the instrument operates with a dedicated cassette. The instrument here can be pre-programmed to know which connectors connect to which ports of the dedicated cassette. Here, the cassette RFID tag may not be needed. The solution RFID tags are still used however to ensure that the correct solutions are connected to the connect cassette port. As shown below, the auto-identification system of the present disclosure operates in one embodiment with an auto-connection mechanism. The auto-connection mechanism automatically connects the supply, patient and drain connectors to the disposable cassette. The mechanism provides a logical place for the auto-identification apparatus as shown below.

The antennae and associated electronics in one embodiment are placed in the dialysis instrument. Alternatively, one or both of the antennae and the associated electronics are located remotely from the instrument. This is possible for example if the cassette has prefixed lines that terminate at connectors (e.g., spiked or sealed membrane connectors). The cassette connectors are loaded into a remote RFID unit. The mating bag and patient connectors having the RFID tags are also fitted to the remote mechanism. Connection is made manually, e.g., via a mechanism that spikes each supply connector in one manual operation. Remote antennae would read the remote tags and relay information to the instrument either wirelessly or via hardwire.

Additional features and advantages are described herein, and will be apparent from, the following Detailed Description and the figures.

DETAILED DESCRIPTION

Referring now to the drawings and in particular to FIGS. 1A to 1C, 2, 3A and 3B, a renal failure therapy system 10 is provided. System 10 is applicable generally to include any type of renal failure therapy system, such as peritoneal dialysis ("PD"), hemodialysis ("HD"), hemofiltration ("HF"), hemodiafiltration ("HDF") and continuous renal replacement therapy ("CRRT"). The auto-identification portion of the system is also applicable to medical delivery in general.

Figure 3A:
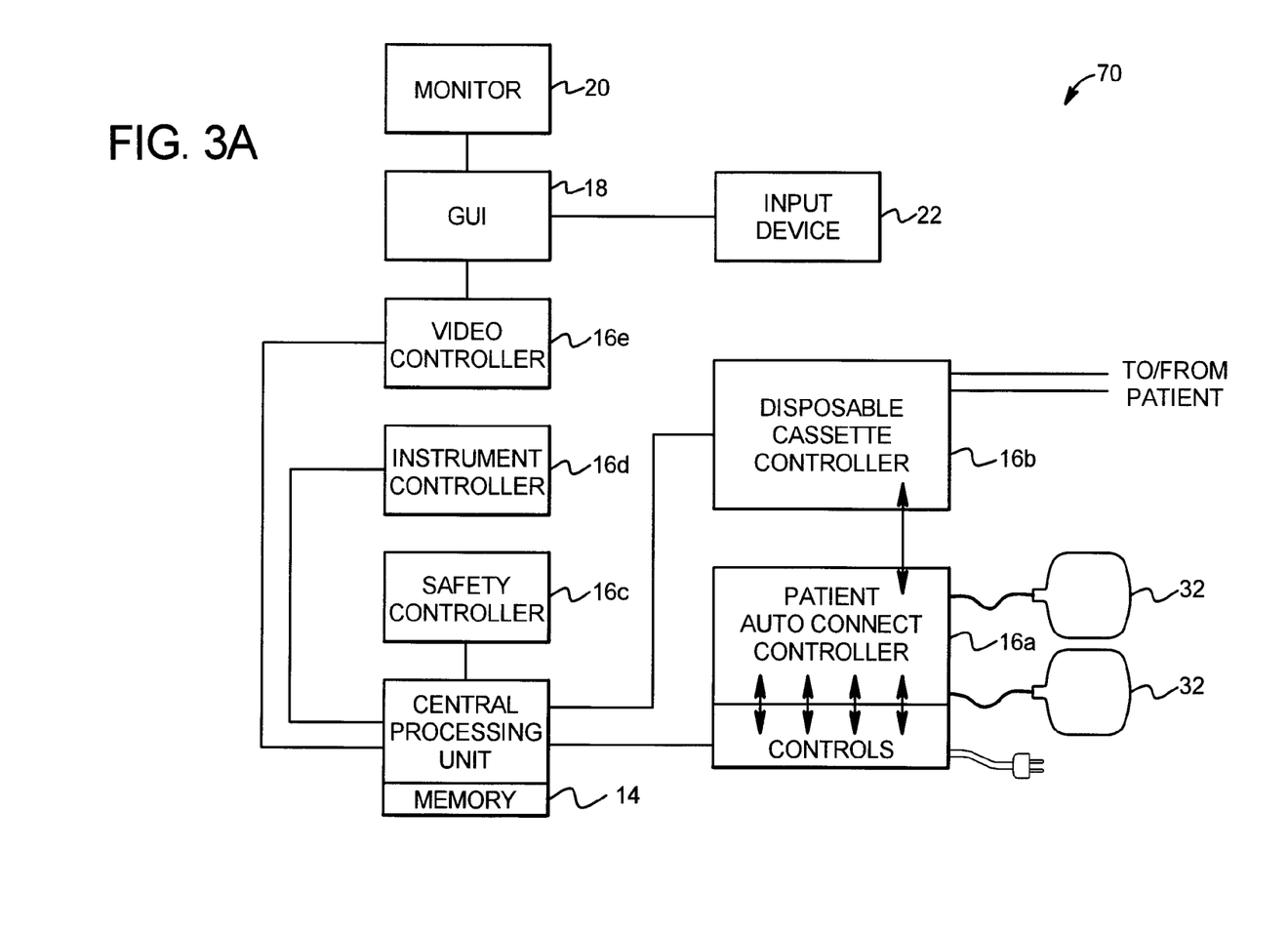
FIGS. 3A and 3B are a schematic illustrations of an embodiment of a control scheme for the renal failure therapy system including control of the RFID apparatus.

System 10 in the illustrated embodiment includes a dialysis instrument 12. Dialysis instrument 12 is configured for whichever type of renal failure therapy or medically delivery system is used. Dialysis instrument 12 as seen in FIG. 3A includes a central processing unit ("CPU") 14 and a plurality of controllers 16a to 16e (more or less controllers can be provided) operable with central processing unit 14. Central processing unit 14 also operates with a graphical user-machine interface ("GUI") 18, e.g., via a video controller 16e, which includes a video monitor 20 and one or more type of input device 22, such as a touch screen or electromechanical input device (e.g., membrane switch, see also FIG. 1).

Figure 1A:
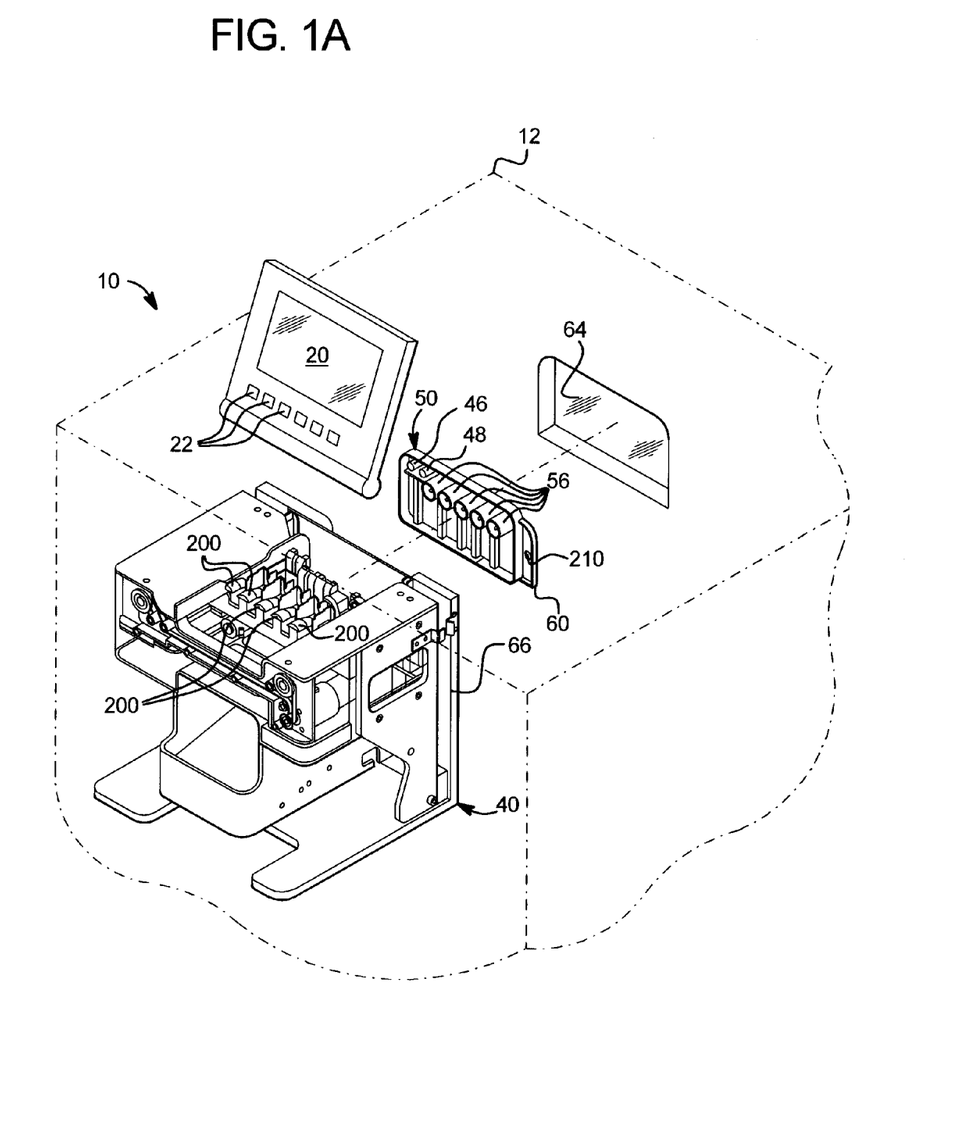
FIG. 1A is a perspective view of an embodiment of a renal failure therapy system employing an auto-connection mechanism, which supports an RFID apparatus of the present disclosure.
Figure 1B:
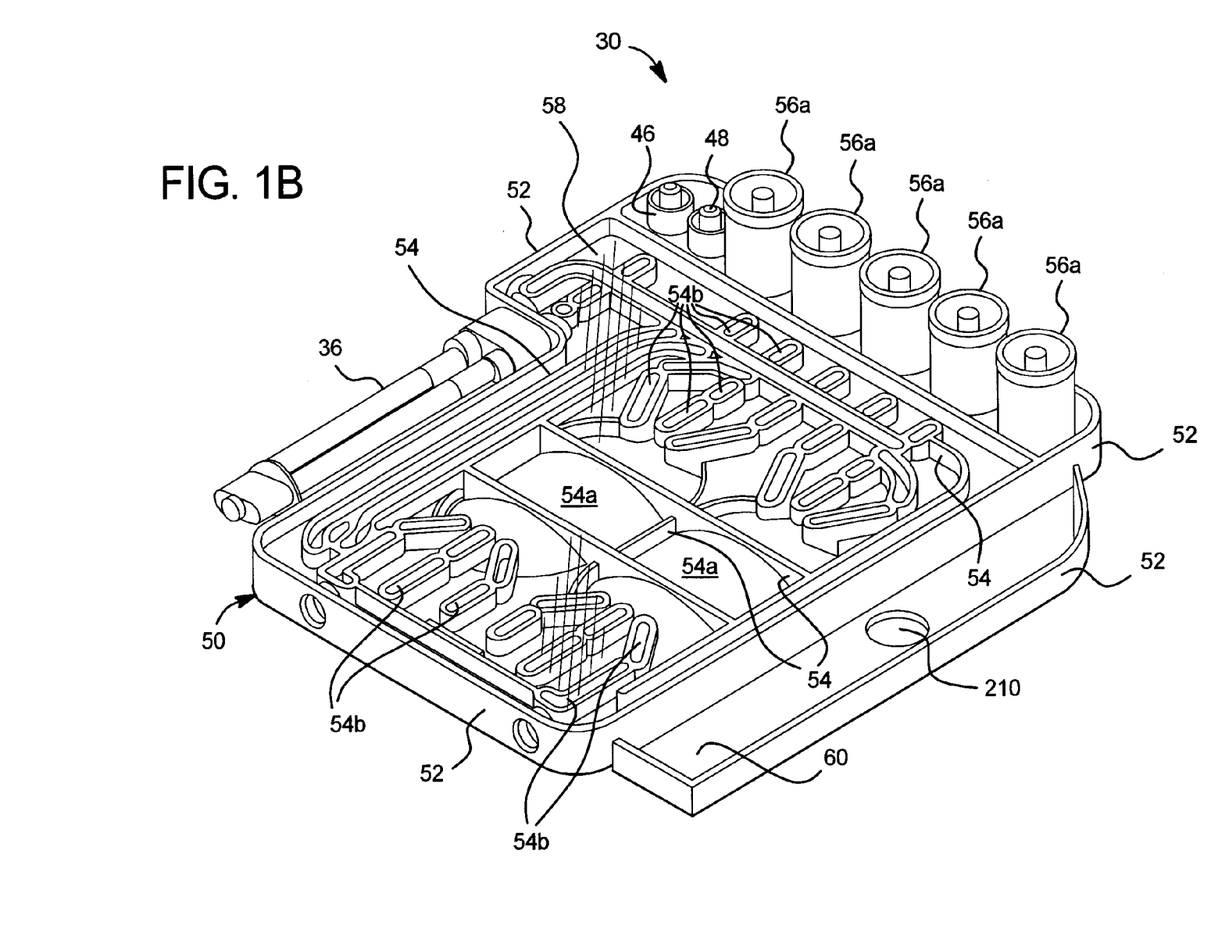
FIG. 1B is a perspective view of an embodiment of a disposable cassette which connects to a supply container solution line shown in FIG. 1C, the cassette including an RFID tag.
Figure 1C:
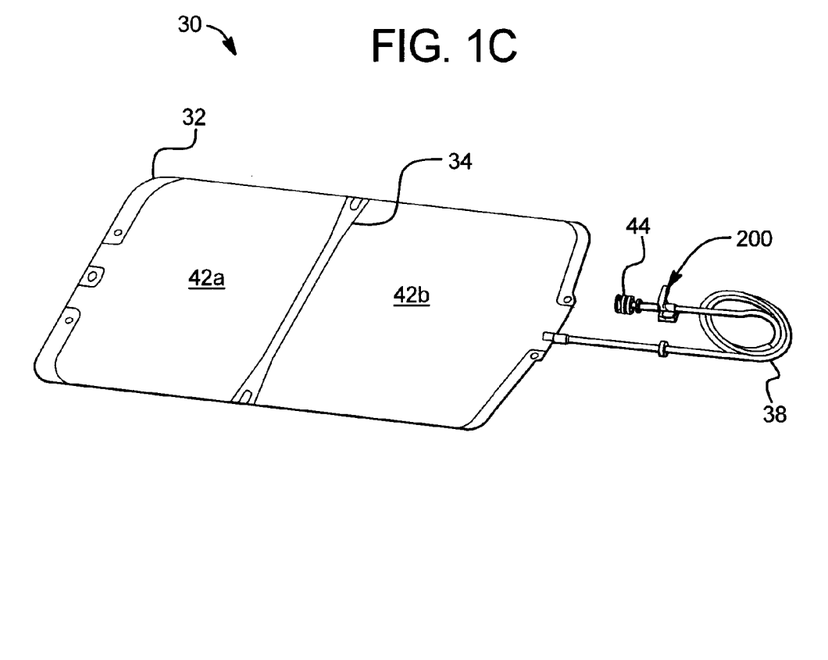
FIG. 1C is a perspective view of an embodiment of a dual chamber bag having a solution line, each of which along with the disposable cassette of FIG. 1B are part of a disposable set of the renal failure therapy system of FIG. 1A.

As seen in FIGS. 1A to 1C, dialysis instrument 12 accepts and operates with a disposable set 30. Disposable set 30 can include one or more supply bag 32 shown here as a dual-chamber supply bag separating two fluids via a peel or frangible seal 34. Disposable set 30 can also include a drain bag (not illustrated), bag tubes 38 and a disposable pumping/valve cassette 50 (FIGS. 1A and 1B). Depending on the type and structure of the renal failure therapy system 10, one or more of the items of disposable set 30 may not be needed. For example, system 10 can pump spent fluid to a house drain, such as a toilet or sink, instead of to drain bag.

Figure 6:
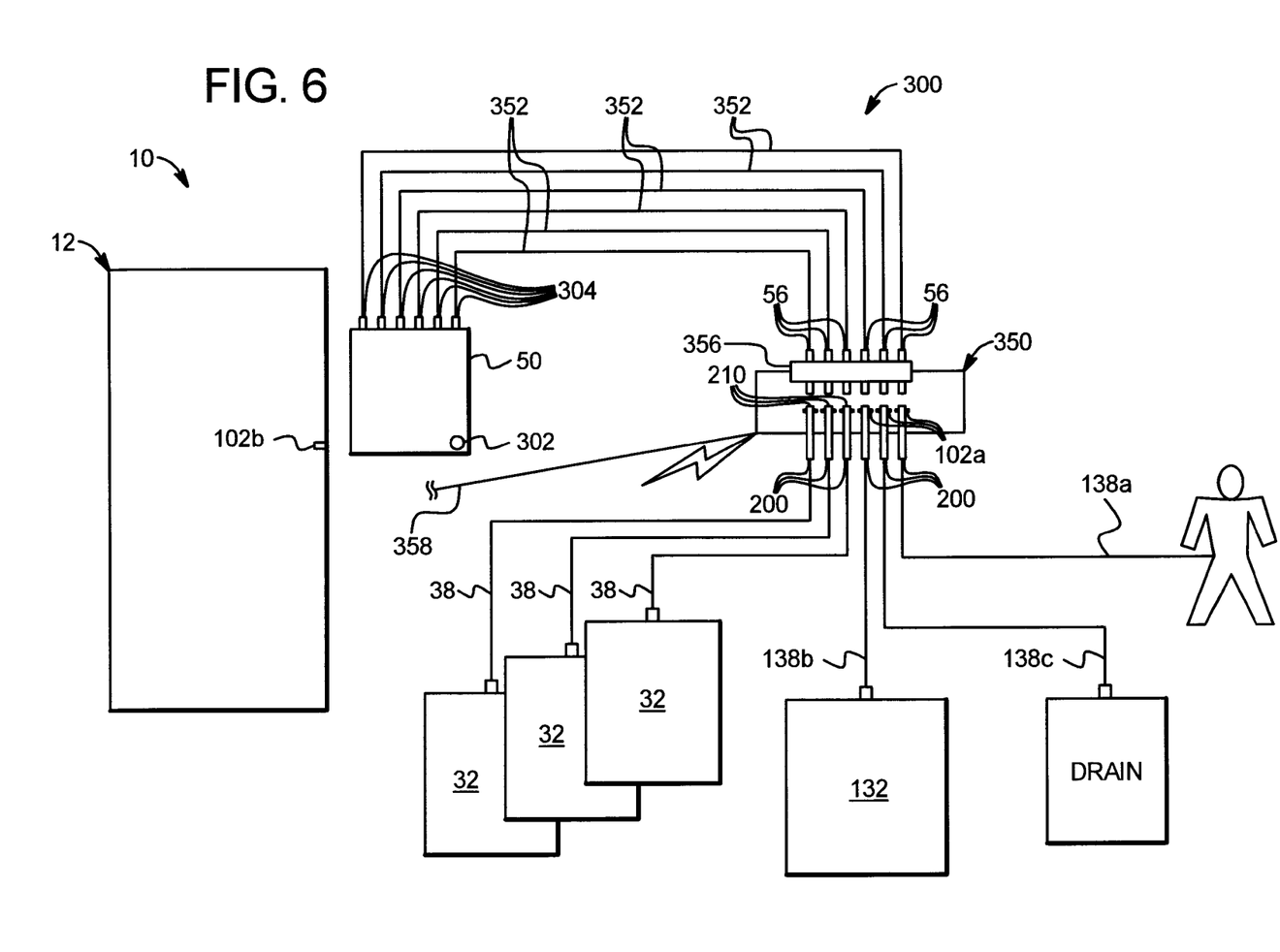
FIG. 6 illustrates one possible embodiment for a remote RFID unit.

FIG. 1B illustrates that that cassette 50 in one embodiment is connected to an inline heater 36 operable with instrument 12. FIG. 6 illustrates an alternative embodiment in which instrument 12 operates via batch heating that heats dialysis fluid in a warmer bag 132. Here, inline heater 36 is not used and an additional connection for warmer bag 132 is made at the cassette.

System 10 can employ any suitable number of supply bags. Supply bag 32 in FIG. 1C is shown having multiple chambers 42a and 42b, separated by frangible seal 34, which hold different solutions depending on the type of therapy employed. For example, chambers 42a and 42b can hold buffer and glucose for PD or and acetate and bicarbonate solution for HD. Supply bags 32 are alternatively single chamber bags, which hold a single solution, such as lactate or acetate.

Cassette 50 connects to supply bags 32 via pigtails or solution tubes 38, which in the illustrated embodiment are provided with the bags. This configuration allows the connection between supply bags 32 and cassette 50 to be made at the cassette, which is loaded into instrument 12. Making the connection at the loaded cassette allows a solution connector integral with or connected to an RFID housing 200 described below to be brought to instrument 12 just prior to connection. The auto-identification system of the present disclosure uses this connection advantageously to allow the RFID antennae to be located in the instrument 12, while the RFID tag that is detected is integral to or mated with the solution connector. Thus each connector and each corresponding bag or container 32 can be interrogated at instrument 12 just prior to connection with cassette 50. If a problem arises, system 10 alarms and takes evasive action before any disposable component is compromised.

Copending, commonly owned patent application Ser. No. 11/773,523, entitled, "Fluid Delivery System With Autoconnect Features", filed Jul. 5, 2007, the entire contents of which are incorporated herein by reference and relied upon, discloses an auto-connection system shown herein generally as auto-connection mechanism 40. As shown herein, auto-identification apparatus 100 is housed within auto-connection mechanism 40. Auto-connection mechanism 40 provides a convenient place to house auto-identification apparatus 100 because as seen in FIG. 1A, RFID housings 200 are loaded into auto-connection mechanism 40 for their connection to cassette 50. Accordingly, as seen in connection with FIGS. 3A and 3B, controls for auto-identification apparatus 100 have been incorporated into the controls of auto-connection mechanism 40.

It should be appreciated first off that the teachings associated with auto-identification apparatus 100 do not require cooperation with an auto-connection mechanism. Also, auto-identification apparatus 100 does not require that the bag to cassette connections be made at the cassette. FIG. 6 shows one example of a bag to cassette connection and associated auto-identification apparatus operating remotely from instrument 12.

Figure 4:
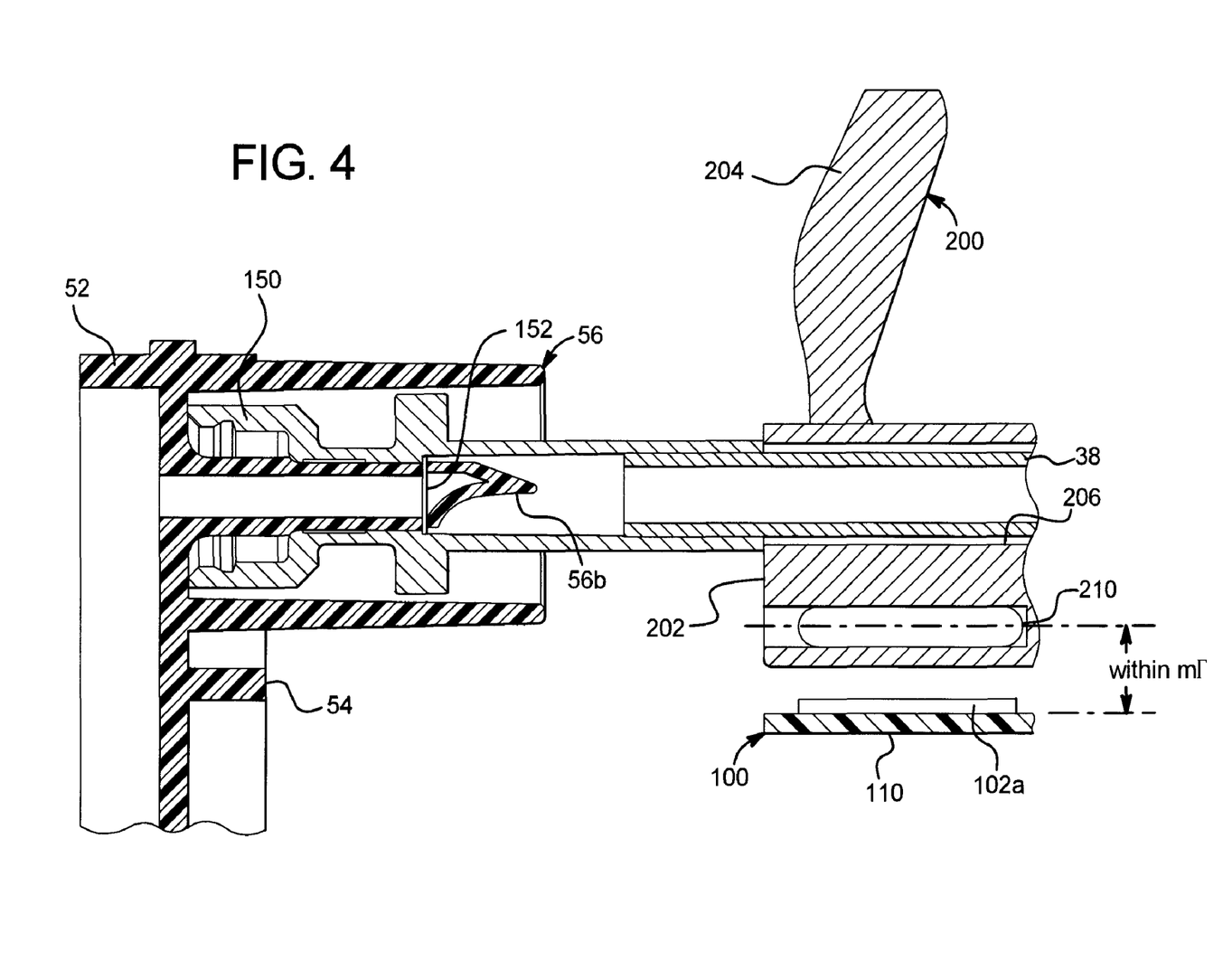
FIG. 4 is a side-sectioned view showing the solution connector having the RFID tag in operable communication with an antenna of the RFID apparatus, the solution connector also shown connected to a supply port of the disposable cassette.
Figure 5:
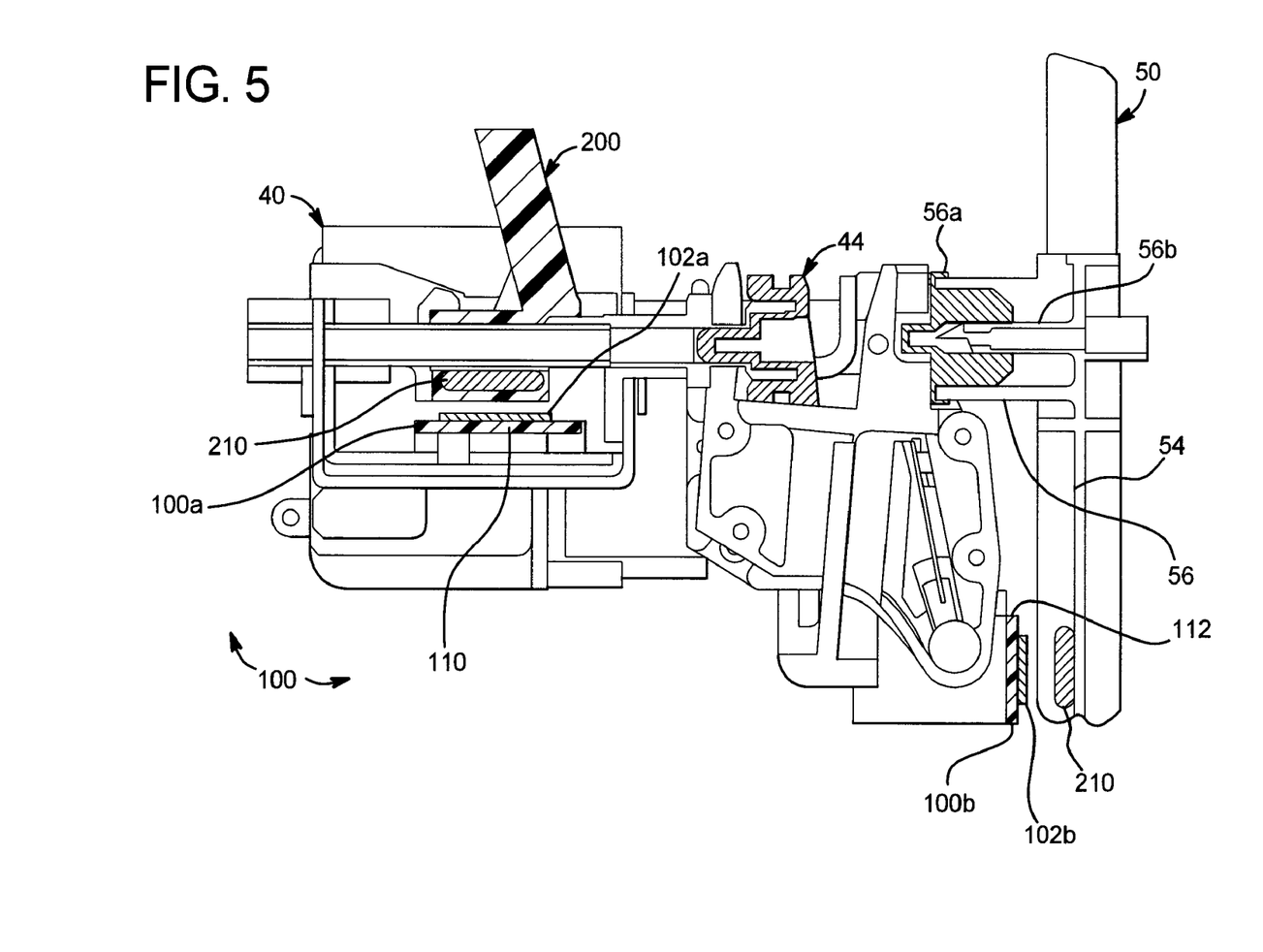
FIG. 5 is a side sectioned view of one embodiment of the auto-connection mechanism in operable communication with a disposable cassette, the RFID apparatus shown mounted in the auto-connection mechanism and in operable communication with both solution connector RFID tags and cassette RFID tag.

Referring additionally to FIGS. 4 and 5, cassette 50 in general includes a rigid structure having rigid outer walls 52, rigid inner walls 54 defining inner pump chambers 54*a* (backside of cassette 50 shown in FIGS. 1A and 1B), fluid pathways 54*b* (front and back of cassette 50) and valve chambers (on opposite side of cassette 50 as shown in FIGS. 1A and 1B). Cassette 50 in the illustrated embodiment includes supply ports 56. FIG. 1B illustrates supply ports 56 having caps 56*a*, which auto-connection mechanism 40 removes at the time bag 32 is connected to cassette to 50. FIG. 4 shows that when cap 56*a* is removed, a spike 56*b* of supply port 56 is exposed. The sectioned view of FIG. 5 shows supply port 56 having cap 56*a* and spike 56*b*.

Cassette also includes a patient port 46 and a drain port 48. Patient port 46 connects to a patient line connected to the patient. Drain port 48 connects to a drain line running to a drain bag or a house drain. As discussed in more detail below, auto-identification apparatus 100 allows system 10 to operate with different cassettes for different modalities. For example, a different cassette having two patient ports 46 for a continuous or multi-pass therapy can be used alternatively.

Cassette 50 also includes flexible sheeting 58 welded to each side of the cassette at rigid outer walls 52. In an embodiment, sheeting 58 is made of polyvinyl chloride ("PVC") and rigid portion is made of acrylic. A plate 66 (FIG. 1A) of auto-connection mechanism 40 mechanically and/or pneumatically presses cassette 50 against a flexible membrane 64 of instrument 12. This action seals sheeting 58 on each side of cassette 50 to respective pump chambers 54a, valve chambers and flow paths 54*b* defined by inner rigid walls 54 of cassette 50. U.S. Pat. No. 4,826,482 ("The '482 Patent"), the entire contents of which are incorporated herein by reference, discloses a pumping system in which a cassette interface plate (not seen) is located behind membrane 64. The cassette interface plate is configured to apply positive or negative pressure to the membrane 64 and cassette sheeting 58, which operate together, at the different valve and pump areas to open and close valves and pump dialysis fluid.

Figure 2:
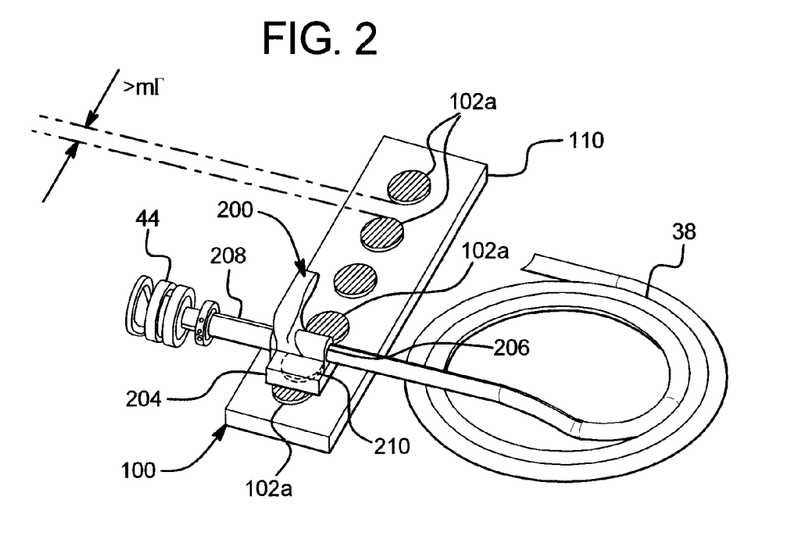
FIG. 2 is a perspective view of an embodiment of an RFID apparatus having multiple RFID antennae, one of which is shown in operable communication with an RFID tag associated with a connector located at an end of the solution line connected to the dual chamber bag.

FIG. 2 illustrates radio frequency identification ("RFID") apparatus 100 in more detail. In one embodiment, as discussed, RFID apparatus 100 is housed in auto-connection mechanism 40. RFID apparatus 100 includes a base 110 onto which RFID antennae 102*a* are mounted. Base 110 can be made of an electrically insulating material, such as plastic or FR-4 material. Antennae 102*a* can be press-fit, molded to or adhered to base 110.

The spacing of antennae 102*a* both with respect to each other and to RFID tags 210 is discussed in detail below. FIG. 2 shows five antennae 102*a*. In this illustrated embodiment, RFID apparatus 100 only identifies supply bag connections associated with the five supply ports 56 of cassette 50. It is important for various reasons to verify that the correct solution container 32 has been connected to the correct supply port 56 as discussed herein. It is expressly contemplated however to additionally provide RFID housing 200 having a RFID tag 210 with either one or both the patient line and the drain line. In an embodiment, a sheet of plastic or other protective cover (not shown) is placed over base 110 and antennae 102*a* of RFID apparatus 100, which prevents the electronics associated with mechanism 100 from being damaged in the case, for example, from a leaking cassette 50. RFID apparatus 100 is configured to read data provided in a machine readable format using RFID technology discussed in detail below.

Figure 3B:
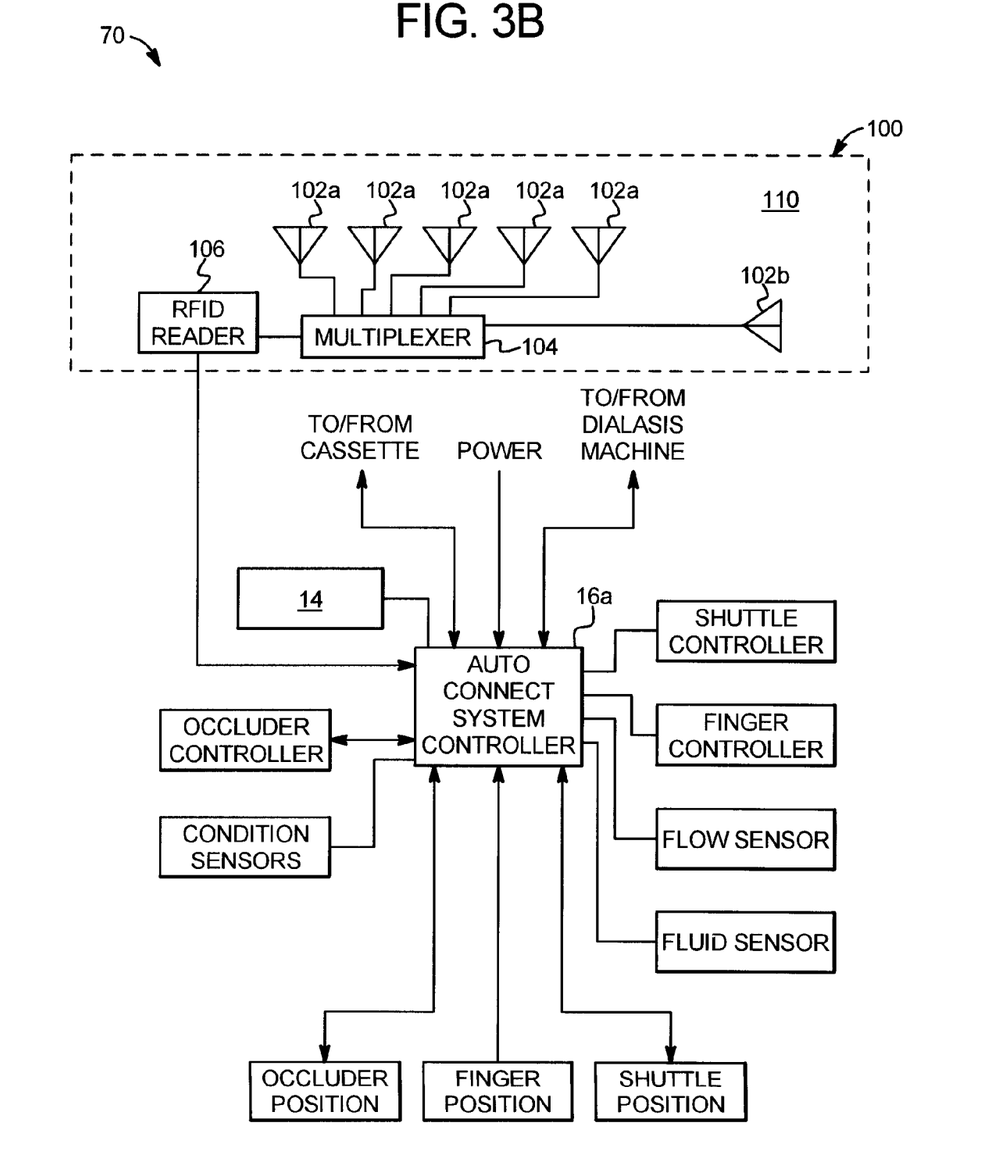

Referring now to FIGS. 3A and 3B, an embodiment of a control scheme 70 for system 10, auto-connection mechanism 40 and RFID apparatus 100 is illustrated. FIG. 3A shows that CPU 14 (which can be redundant CPU's) communicates with many delegate controllers, such as auto-connect controller 16*a*, cassette controller 16*b* (which can also communicate with one another), safety controller 16*c*, instrument controller 16d and video controller 16*e*. FIG. 3B illustrates that auto-connect controller 16*a* operates with a plurality of sub-controllers and sensors, including an RFID reader 106. Again, the auto-identification system does not have to operate under an auto-connection system, such that RFID reader 106 could communicate alternatively with CPU 14 or with another controller communicating with CPU 14. In any case, communication between RFID reader 106 and electronics within instrument 12 can be hardwired communication or wireless communication (e.g., wireless radio frequency ("RF") interface). FIG. 6 illustrates wireless communication in more detail.

The circuitry and reader 106 for RFID mechanism 100 in one embodiment are placed on the same base 110 as are antennae 102*a*, e.g., onto an printed circuit board ("PCB"). Alternatively, the circuitry and reader 106 of RFID mechanism 100 one located on a PCB with auto-connect controller 16*a* and any one or more of the auto-connection components of FIG. 3B. Antennae 102 can for example be configured into a trace pattern on PCB 110 as illustrated. In the illustrated embodiment, antennae 102 are connected to multiplexer 104. Multiplexer 104 in turn is connected to RFID reader or interrogator 106. RFID reader 106 communicates with antennae 102 through multiplexer 104. Alternatively, multiplexer 104 selects one of the antennae 102*a* as a data-source, which outputs data to RFID reader 106. Multiplexer 104 functions as a multiple-input, single-output switch. Each antennae 102*a* inputs data to multiplexer 104, which outputs the data to RFID reader 106.

RFID reader 106 or other component of auto-connect controller 16*a* can include processing and electronics configured to control multiplexer 104 to sequence through antennae 102*a* and 102*b* in a way such that auto-connect controller 16*a* knows at any given relevant time which antenna 102*a* or 102*b* is being interrogated. For example, each antenna 102*a* or 102*b* could be assigned an address, e.g., 001 to 006. When multiplexer 104 is caused to interrogate the antenna at address 001, auto-connect controller 16*a* knows which supply port 56 of cassette 50 is being interrogated. This information is compared against the information that the antenna at address 001 receives from whichever RFID tag 210 is mated with antenna at address 001. The comparison may be done at RFID reader/interrogator 106, auto-connect controller 16*a* or CPU 14 as desired. When multiplexer 104 is caused to interrogate the antenna at address 002, the procedure described for antenna at address 001 is repeated, and so on.

Alternatively, RFID apparatus 100 does not use multiplexer 104. For example, RFID reader 106 can be configured to communicate with each antennae 102 at a different frequency. Antenna 102*a* emits information at a first frequency, antenna 102*b* at a second frequency and so on, so that RFID reader 106 knows which antenna is sending information at a given point in time. RFID reader 106 can store an identification code for each frequency, i.e., each antenna 102, such that RFID reader 106 can thereafter communicate with higher lever controllers 16*a* and 14 using the codes and any associated tag information read by the coded antenna. In this embodiment, multiple antennae can be read at the same time and each antenna can be read at any relevant time (e.g., at the beginning of treatment when connections are made or at the end of treatment when bags 32 are disconnected from cassette 50).

RFID apparatus 100 operates with RFID tags 210, which are sometimes termed "smart tags" or "smart labels". It is believed that at least Datamrs Inc., Peachtree City, Ga. and RCD Technology Corporation, Quakertown, Pa. can provide RFID tags 210 suitable for the application described herein, and which can be placed in housing 200 as shown in FIG. 4 for example. RFID tags 210 can provide a large amount of data in a condensed space. Further, RFID tags 210 have very high readability allowing reader 106 to scan the tags regardless of the orientation of the tags with respect to reader 106. Tag data can be erased, appended to or rewritten.

RFID tags 210 offer increased flexibility, privacy and security because tag data can be encoded and/or encrypted. Encoded and/or encrypted information requires proper encoding/encryption and decoding/decryption techniques and/or equipment for access. Further, various encoding and/or encryption techniques allow for the optimization of stored and transferred information. Different forms of data encryption or encoding are available for both reader 106 and tags 210, such as advanced encryption standard ("AES") encryption and secure hash algorithm ("SHA") hashing. The AES encryption scrambles data from tags 210, so that unauthorized machines cannot read tags 210. The SHA hashing protects against the tampering and counterfeiting of tags 210.

Generally, RFID tags include a transponder for communication with reader 106. Different transponders have different read and write functionalities. A transponder can for example be read only ("R/O"), read/write ("R/W") or write once/read many ("WORM"). Different transponders can also have different types of power sources. An active transponder is equipped with battery power, thereby providing greater reading distances, while a passive transponder is powered by the RF energy emitted from reader or interrogator 106.

Transponders of the RFID tags 210 used herein may operate at different frequency ranges. For example, a low frequency transponder typically operates from about 125 kHz to about 134.2 kHz or from about 140 kHz to about 148.5 kHz with a read range of up to about 12 inches. A high frequency transponder typically operates at about 13.56 MHz with a read range of up to about 3 to 4 feet. The transponder may even operate at an ultra-high frequency typically within the range of about 868 Mhz to 928 Mhz and with a read range greater than about 10 feet.

In an embodiment, the RFID tags 210 include passive, R/O, low frequency transponders. RFID tags 210 in an embodiment are about 11 mm (0.43 inch) in diameter. In one embodiment, the RFID tags 210 have a maximum read distance to antennae 102a of about 25 mm (0.98 inch). In another embodiment, the maximum read distance is less than about 20 mm (0.79 inch). Tags 210 can thereby operate at any distance from antennae 102a within the maximum read distance.

For apparatus 100, antennae 102a are spaced apart from each other a distance equal to and preferably greater than the maximum read ("mr") distance as shown in FIG. 2 (not to scale). With antennae 102a spaced apart at a distance equal to or greater than the maximum read distance, each individual antenna 102a reads a unique RFID tag 210 placed in the illustrated embodiment above the corresponding tag 210, at an operating distance within the maximum read distance as shown in FIG. 4 (not to scale). This enables RFID apparatus 100 to identify the location or position of each RFID tag 210 by virtue of knowing the position of each antenna 102a.

Referring to FIG. 4, an embodiment of RFID housing 200 having RFID tag 210 is illustrated. RFID housing 200, includes a body 202 and handle 204. Suitable materials for body 202 and handle 204 include plastic, such as injection molded ABS, Delrin®, Noryl®, polycarbonate or other suitable medical grade plastic. Body 202 defines a lumen 206, which accepts one of the solution tubes 38 (or patient, drain or warmer bag tube as required). Solution tube 38 as illustrated is mechanically and/or adhesively bonded to a female supply connector 150 having a pierceable membrane 152. In FIG. 4, supply connector 150 has been connected to one of the supply ports 56 of cassette 50. As seen, spike 56b of the supply port has pierced the membrane 152 of connector 150, establishing fluid communication between the associated supply container 32 and cassette 50.

RFID housing 200 can be mechanically and or adhesively bonded to tube 38 or connector 150 or can be slideably engaged to tube 38. Alternatively, RFID housing 200 holding RFID tag 210 can be formed integrally with supply connector 150. Providing RFID housing 200 separately from connector 150 is advantageous in one respect in that it enables housing 200 to operate with different connectors, e.g., supply connector 150 or a different patient or drain connector. RFID tag 210 can be adhered to, molded into and/or press-fitted into body 202 of housing 200.

Alternatively, RFID tag 210 could be affixed to or embedded into handle 204 or other desirable portion of RFID housing 200. With RFID tag 210 embedded into RFID housing 200, housing 200 can be sterilized via steam or ethylene oxide ("EtO") gas sterilization, for example. Embedding RFID tag 210 into body 202 or otherwise encapsulating RFID tag 210 also helps to protect RFID tag 210.

Tube 38 in the illustrated embodiment is connected to a dual-chamber or multi-chamber supply bag 32. Supply bag 32 stores two or more fluids. RFID tag 210 is encoded with data regarding the fluid (as mixed). For example, RFID tag 210 can be encoded with information regarding the type, quantity and/or lot of fluid as mixed, which is contained in supply bag 32. Alternatively, supply bag 32 is a single chamber bag. Here, it is still important to know the type, quantity and lot of fluid being delivered to the patient. Further alternatively, RFID tag 210 can include type and volume information for a particular concentrate that is mixed at cassette 50 or downstream from the cassette.

Referring now to FIG. 5, auto-connection mechanism 40 housing RFID apparatus 100 is illustrated in more detail. In the illustrated embodiment, RFID apparatus 100 includes a first portion 100a (shown in FIGS. 2 and 4) having antennae 102a stored on base 110 that read RFID tags 210 located within housing 200 as has been discussed herein. Additionally and optionally, RFID apparatus 100 includes a second portion 100b having an antenna 102b stored on a separate base 112 that reads a RFID tag 210 located on cassette 50. Base 112 can be constructed of the same material and in the same manner as base 110.

Cassette 50 as seen additionally in FIGS. 1A and 1B includes a portion 60, which may or may not be covered by sheeting 58, and which holds a RFID tag 210. RFID tag 210 is advantageously positioned away from heater 36. Tag 210 can be adhered to, molded into or press-fitted into portion 60 of cassette 50. It should be appreciated that RFID tag 210 may be affixed to the interior or exterior, rigid or flexible portion of cassette 50 provided it is affixed in a sturdy manner and remains in close proximity to antenna 102b of RFID apparatus portion 100b.

RFID apparatus portion 100b is affixed to auto-connection mechanism 40 such that when cassette 50 is loaded into instrument 12, cassette 50 lays adjacent to RFID apparatus 100b as seen in FIG. 5. As illustrated, RFID apparatus portion 100b includes antenna 102b. Antenna 102b is configured to read RFID tag 210 associated with cassette 50. When cassette 50 is installed, RFID tag 210 lies in close proximity to antenna 102b, within the operating distance of tag 210 of cassette 50.

RFID tag 210 and antenna 102*b* have a maximum read distance of less than about 25 mm (0.98 inch) in one embodiment and less than about 20 mm (0.79 inch) in another embodiment and can have the same characteristics as those described above for antenna 102*a*. RFID tag 210 of cassette 50 is positioned less than the maximum read distance of from antenna 102*b*, within the operating distance of tag 210, when cassette 50 is loaded into the instrument. RFID tag 210 of cassette 50 is also positioned well away from tags 210 of RFID apparatus portion 100*a*, such that only antenna 102*b* can read RFID tag 210 of cassette 50 when the cassette is loaded, providing authenticity information and cassette information for cassette tag 210 and cassette 50.

Cassette tag 210 is encoded with data regarding cassette 50. For example, tag 210 can be encoded with information regarding treatment type, number of supply bags, number of valves, number of pumps, number of cycles, etc., associated with a treatment performed with cassette 50. The cassette type can be used to select pumping, valving and heating algorithms stored in instrument 12. RFID reader 106 also operates with antenna 102*b* as seen in FIG. 3B, reads the above information and sends it to one or more controller to CPU 14. System 10 evaluates the information to determine if the proper cassette has been loaded for a particular therapy, and to potentially set pumping, valving and heating algorithms for the therapy.

System 10 can be configured to interrogate cassette 50 to ensure that a proper cassette has been loaded. If the cassette is improperly loaded, CPU 14 sends a command to video controller 16*e*, which causes GUI 18 to display a message, such as an error and/or instructional message, on video monitor 20. Although not illustrated, the instrument can be equipped with speakers and sound or voice activation to sound an alarm or to verbalize an alarm and/or a corrective action. The visual or audible alarm alerts the patient, a medical care provider (e.g., doctor or registered nurse) or a non-medical care provider (e.g., family member or friend) of the need to address, for example, an error or to read an instructional message on video monitor 20. Alternatively, if the proper cassette 50 has been loaded, CPU 14 enables treatment to proceed without displaying a message or verbalizing an alarm/alert.

In one embodiment, the encoded information of cassette tag 210 is encrypted. RFID apparatus 100 can then be used to prevent the use of fraudulent or copied cassettes. Cassette tag 210 can also be encoded with information regarding how many supply bags 32 to load to the cassette, whether the cassette requires one or two patient lines, or which fluid port 56 should be connected to which type of concentrate for a particular cassette 50. It is thereby contemplated to provide a system 10 having an instrument 12 capable of accepting a first cassette configured for a first treatment modality and a second cassette configured for a second modality. For example, the instrument 12 can accept a first cassette configured for batch peritoneal dialysis using a single patient line and a second cassette configured for continuous or multiple-pass dialysis using two patient lines.

Antennae 102*a* of RFID apparatus portion 100*a* are positioned to read RFID tags 210 of housings 200 associated with supply connectors 150. Each antenna 102*a* is associated with one housing 200 and thus one connector 150 and one supply port 56. As discussed, each antenna 102*a* lies less than a maximum read distance from its associated housing 200 when housings 200 are placed into auto-connection mechanism 40. Further, antennae 102*a* are positioned such that they lie at least the maximum distance from each other when housings 200 are placed into auto-connection mechanism 40. Thus, each antenna 102*a* will be able to read only one RFID tag 210 just prior to medical connectors 150 being connected to cassette supply ports 56. If the auto-identification system detects a problem with one of the connectors 150 loaded into auto-connection mechanism 40, e.g., improper solution at an improper location, the problem is detected before an associated connector 150 is spiked, saving the solution in the associated bag 32 and likely saving the cassette 50 as well, both of which would likely have to be discarded.

Solution tags 210 and antennae 102*a* ensure that the proper fluid in the proper amount flows to and from the proper source and destination as discussed above. If a problem is detected, CPU 14 sends a command to video controller 16*e* based on the processed information from solution tags 210. Video controller 16*e* causes GUI 18 to display a message, such as an error and/or instructional message, on video monitor 20 that one or more solution container has been loaded into auto-connection mechanism 40 improperly. Although not illustrated, instrument 12 can be equipped with speakers and sound or voice activation to sound an alarm or to verbalize an alarm and/or a corrective action. The visual and/or audible alarm alerts the patient, a medical care provider (e.g., doctor or registered nurse) or a non-medical care provider (e.g., family member or friend) of the need to address, for example, an error or to read an instructional message on video monitor 20. Alternatively, if each of the supply containers 32 is loaded properly into mechanism 40, CPU 14 enables connectors 150 to be spiked and treatment to proceed without displaying a message or verbalizing an alarm/alert.

In an embodiment, the encoded information of each solution RFID tag 210 is encrypted. RFID apparatus 100 can then be used to prevent the use of third party fluids, tubing, and/or connectors.

Optional cassette tag 210 and solution tags 210 enable system 10 to perform a two-stage analysis. Cassette tag 210 enables system 10 to determine that a particular cassette of a plurality of possible cassettes has been properly loaded into instrument 12. Solution tags 210 then enable system 10 to determine, for the particular cassette, whether a proper solution has been placed into a proper position for mating with the proper supply port 56 of cassette 50.

It should be appreciated that system 10 is configured alternatively such that instrument 12 can only accept one cassette. Here, cassette tag 210 may not be needed or provided. Instead, the electronics (local to mechanism 100 or at CPU 14) are preconfigured to know which housing 200/connector 150 is to be connected to which port 56 of cassette. Here, the output of RFID reader 106 is processed and compared to the order preset in memory to determine if each housing 200/connector 150 has been connected correctly.

As alluded to above, RFID tags 210 and associated antennae 102*a* are not limited to use with solution lines 38 and supply connectors 150. Housing 200 and tags 210 can additionally be used with the loading and connection of a drain line into auto-connection mechanism 40 and the loading and connection of one or more patient line into auto-connection mechanism 40. For example, it is expressly contemplated to place RFID housing 200 having a RFID tag 210 on the patient line to detect whether the patient line is a standard adult patient line or a pediatric patient line, which typically has a smaller inner diameter to restrict flow. It is also beneficial to know that the patient line has been placed into the correct position for priming purposes.

Fluid has to flow through the patient line to reach the patient. The patient line therefore provides an opportune checking point to ensure that the type and amount of fluid to be delivered to the patient are prescribed or within a range of prescribed limits. It is therefore expressly contemplated to encode the RFID tag 210 associated with the patient line and patient connector with information identifying the patient. System 10 then checks the solution bags that are about to be connected to cassette 50 and the therapy parameters set at instrument 12 to ensure that the solutions and parameters are prescribed or fall within prescribed limits for the particular patient. This check is not only useful for safety reasons, but is also useful for machines used by multiple patients to know which patient is connected. Suitable alarms/corrective action can be made as described above if a problem occurs.

FIGS. 1A, 4 and 5 illustrate RFID apparatus 100 located within dialysis instrument 12. FIG. 6 illustrates an alternative RFID system 300, in which RFID apparatus 350 is located remotely from instrument 12. Here, spike connectors 56 are attached at one end of cassette tubes 352, which are pre-fitted to ports 304 on the cassette 50. Connectors 56 can be banded together in an organizer 356, which is inserted into remote apparatus 350. RFID housings 200/connectors 150 in the illustrated embodiment are inserted into remote apparatus 350 individually or via an organizer 356 to mate with one of spike connectors 56.

Apparatus 350 can include a loading feature that prevents spiking (either manual or automatic) until each tag 210 is verified. If a problem is detected, apparatus 350 sends a signal to instrument 12, which alarms/alerts as described above. If each tag 210 is verified, the locking device unlocks and the associated connectors can be spiked or otherwise connected (either manually or automatically).

In any embodiment discussed herein, the connector associated with RFID housing 200 can be a spike connector or a pierceable female connector, that is, RFID housings 200 do not have to be associated with female connectors 150. FIG. 6 also illustrates that RFID tags 210 can be used to identify that a patient line 138a, warmer bag line 138b (warmer bag 132 used in place of inline heater 36 shown above) and drain line 138c have been loaded into a proper position relative to connectors 56 and cassette 50.

In the remote embodiment, connector antennae 102a are located within remote apparatus 350. Cassette antenna 102b, if provided, is still located within instrument 12, which operates with RFID tag 210 of cassette 50 as described above. Alternatively, cassette tag 210 and antenna 102b are not used as described above. Remote apparatus 350 includes the autoconnection electronics described above in connection with FIG. 3B and communicates remotely (as shown by the energy bolt design) or via hardwire (as shown alternatively via cable 358) with instrument 12 and the remainder of electrical scheme 70 shown above in FIGS. 3A and 3B. Each of the functional embodiments (e.g., two-stage decision making or single stage decision making) described above is applicable with the remote configuration for RFID apparatus 350 of system 300.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical fluid delivery system comprising:
   a dialysis instrument;
   a disposable pumping cassette operable with a pumping actuator of the dialysis instrument, the disposable cassette including or connected fluidly to a plurality of first connectors;
   a plurality of second connectors configured to interface with the first connectors, each of the plurality of second connectors connected to a fluid conduit and configured to be attached to an auto-connection mechanism;
   a plurality of housings, each of the plurality of housings carrying a radio frequency ("RFID") tag, each second connector associated with one of the RFID tags; and
   electronics positioned on the autoconnection mechanism, the electronics configured to read the RFID tags via a plurality of antennae and to identify that each of the second connectors is positioned properly with respect to a proper one of the first connector,
   wherein the autoconnection mechanism is configured to cause the plurality of second connectors along with the respective fluid conduits to be connected to the plurality of first connectors, and wherein the electronics are further configured to identify a position of each second connector relative to its respective first connector prior to the autoconnection mechanism connecting the second connectors to the first connectors.

2. The medical fluid delivery system of claim 1, wherein at least one of the RFID tags is encoded with information pertaining to at least one of: (i) type of solution in a supply container connected to the corresponding second connector; (ii) volume of the supply container; (iii) that one of the second connectors is a patient line connector; (iv) that one of the second connectors is a drain line connector; and (v) that one of the second connectors is a warmer bag connector.

3. The medical fluid delivery system of claim 1, wherein the electronics are preset to know which second connector should be connected to which first connector.

4. The medical fluid delivery system of claim 1, wherein the antennas are positioned within the instrument or in a unit communicating with the instrument.

5. The medical fluid delivery system of claim 1, wherein the disposable cassette includes an RFID tag encoded with information regarding the disposable cassette and readable via one of the antennas.

6. The medical fluid delivery system of claim 5, wherein the information regarding the disposable cassette is encrypted.

7. The medical fluid delivery system of claim 5, wherein the electronics are configured to use the cassette RFID tag to determine a type of cassette loaded into the instrument and to use the second connector RFID tags to determine that the second connectors have been connected to the type of cassette properly.

8. The medical fluid delivery system of claim 1, wherein the antennae are positioned at least a maximum read distance apart, each antenna positioned less than the maximum read distance from one of the first connectors.

9. The medical fluid delivery system of claim 1, wherein at least one of: (i) the first connectors are ports extending from the disposable cassette; (ii) the second connectors communicate fluidly with a solution container; (iii) one of the second connectors is a patient or drain line connector; (iv) the RFID tags are separate from the second connectors; and (v) the RFID tags are integrated with the second connectors.

10. A medical fluid delivery system comprising:
    a dialysis instrument;
    a disposable pumping cassette operable with a pumping actuator of the dialysis instrument, the disposable cassette including or connected fluidly to a plurality of first connectors;
    a plurality of second connectors, each second connector associated with a radio frequency identification ("RFID") tag, connected to a fluid conduit and configured to be attached to an autoconnection mechanism, the tags physically separate from the second connectors and defining a maximum read distance, each second connector configured to interface with one of the first connectors;

a plurality of antennae positioned on the autoconnection mechanism and at least a maximum read distance apart, each antenna associated with and positioned less than the maximum read distance from one of the RFID tags; and electronics positioned on the autoconnection mechanism and operable with the antennae to identify a position of each of the second connectors relative to their respective first connector, wherein the autoconnection mechanism is configured to cause the plurality of second connectors along with the respective fluid conduits to be connected to the plurality of first connectors, and wherein the electronics are operable with the antennae to identify a position of each second connector relative to its respective first connector prior to the autoconnection mechanism connecting the second connectors to the first connectors.

11. The medical fluid delivery system of claim 10, wherein at least one of the RFID tags is encoded with information pertaining to at least one of: (i) a type of solution in a supply container connected to the corresponding second connector; (ii) volume of the supply container; (iii) one of the second connectors being a patient line connector; (iv) one of the second connectors being a drain line connector; and (v) one of the second connectors being a warmer bag connector.

12. The medical fluid delivery system of claim 10, which is preset to know which second connector should be connected to which first connector.

13. The medical fluid delivery system of claim 10, wherein the antennas are positioned within the instrument or in a unit communicating with the instrument.

14. The medical fluid delivery system of claim 10, wherein the disposable cassette includes an RFID tag encoded with information regarding the disposable cassette and readable via one of the antennas.

15. The medical fluid delivery system of claim 14, wherein the information regarding the disposable cassette is encrypted.

16. The medical fluid delivery system of claim 14, wherein the electronics are configured to use the cassette RFID tag to determine a type of cassette loaded into the instrument and to use the connector RFID tags to determine that the second connectors have been connected to the particular type of cassette properly.

17. The medical fluid delivery system of claim 10, wherein at least one of: (i) the first connectors are ports extending from the disposable cassette; (ii) the second connectors communicate fluidly with a solution container; (iii) one of the second connectors is a patient or drain line connector; and (iv) the RFID tags are integrated with the second connectors.

18. A medical fluid delivery system comprising:
a medical instrument;
a plurality of first connectors in communication with a pumping actuator of the medical instrument;
a plurality of second connectors configured to interface with the first connectors, each second connector associated with and physically separate from a radio frequency identification ("RFID") tag, each of the plurality of second connectors connected to a fluid conduit and configured to be attached to an autoconnection mechanism;
a plurality of antennae housed within the autoconnection mechanism, each antenna positioned adjacent to one of the first connectors, the antenna spaced apart so that each antenna is able to detect only one of the RFID tags; and
electronics operable with the antennae to identify a position of each of the second connectors relative to the first connectors,
wherein the autoconnection mechanism is configured to cause the plurality of second connectors along with the respective fluid conduits to be connected to the plurality of first connectors, and wherein the electronics are configured to identify a position of each second connector relative to its respective first connector prior to the autoconnection mechanism connecting the second connectors to the first connectors.

19. The system of claim 18, wherein the electronics includes at least one of an RFID reader and a multiplexer.

20. The medical fluid delivery system of claim 18, wherein at least one of the RFID tags is encoded with information pertaining to at least one of: (i) a type of solution in a supply container connected to one of the second connectors; (ii) volume of the supply container; (iii) one of the second connectors being a patient line connector; (iv) one of the second connectors being a drain line connector; and (v) one of the second connectors being a warmer bag connector.

21. The medical fluid delivery system of claim 18, wherein the electronics are configured to know which second connector should be connected to which first connector.

22. The medical fluid delivery system of claim 18, wherein the medical instrument is selected from the group consisting of an infusion pump instrument and a dialysis instrument.

23. The medical fluid delivery system of claim 18, wherein the electronics are positioned within the medical instrument or in communication with the medical instrument.

24. The medical fluid delivery system of claim 18, wherein at least one of: (i) the first connectors are ports extending from the disposable cassette; (ii) the second connectors communicate fluidly with a solution container; and (iii) one of the second connectors is a patient or drain line connector.

25. The medical delivery system of claim 1, wherein each of the plurality of housings includes a handle, and wherein each of the RFID tags is located within the handle of the housing.

26. The medical delivery system of claim 1, wherein each of the plurality of housings is releasably attached to one of the fluid conduits.

* * * * *

UNITED STATES PATENT AND TRADEMARK OFFICE
CERTIFICATE OF CORRECTION

Page 1 of 1

PATENT NO. : 8,330,579 B2
APPLICATION NO. : 11/773822
DATED : December 11, 2012
INVENTOR(S) : Kneip et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1272 days.

Signed and Sealed this
Twenty-first Day of February, 2023

Katherine Kelly Vidal
*Director of the United States Patent and Trademark Office*